(12) United States Patent
Fox et al.

(10) Patent No.: US 7,859,749 B2
(45) Date of Patent: Dec. 28, 2010

(54) CONFOCAL MICROSCOPE FOR IMAGING OF SELECTED LOCATIONS OF THE BODY OF A PATIENT

(75) Inventors: William J. Fox, Rochester, NY (US); Christopher C. DiStasio, Rochester, NY (US); Scott R. Grodevant, Rochester, NY (US)

(73) Assignee: Lucid, Inc., Rochester, NY (US)

( * ) Notice: Subject to any disclaimer, the term of this patent is extended or adjusted under 35 U.S.C. 154(b) by 0 days.

(21) Appl. No.: 12/154,981

(22) Filed: May 29, 2008

(65) Prior Publication Data

US 2008/0239474 A1   Oct. 2, 2008

Related U.S. Application Data

(62) Division of application No. 10/557,461, filed on Nov. 18, 2005, now Pat. No. 7,394,592.

(51) Int. Cl.
*G02B 21/00* (2006.01)
(52) U.S. Cl. ..................................... 359/384; 359/196.1
(58) Field of Classification Search ........................ None
See application file for complete search history.

(56) References Cited

U.S. PATENT DOCUMENTS

| 5,788,639 | A | | 8/1998 | Zavislan et al. |
| 5,820,623 | A | | 10/1998 | Ng |
| 5,861,983 | A | * | 1/1999 | Twisselman ................ 359/384 |
| 5,880,880 | A | | 3/1999 | Anderson et al. |
| 5,982,532 | A | | 11/1999 | Mittelstadt et al. |
| 5,995,283 | A | | 11/1999 | Anderston et al. |

(Continued)

FOREIGN PATENT DOCUMENTS

CN    1349122 A    5/2002

(Continued)

OTHER PUBLICATIONS

Milind Rajadhyaksha and James M. Zavislan, Confocal Laser microscope images tissue in vivo, Laser Focus World, vol. 33, No. 2 pp. 119-127, Feb. 1997.

(Continued)

*Primary Examiner*—Stephone B Allen
*Assistant Examiner*—Derek S Chapel
(74) *Attorney, Agent, or Firm*—Kenneth J. Lukacher

(57) ABSTRACT

A confocal imaging microscope, especially for the cellular imaging of the skin at selected locations, is ergonomic in use, compact, and positionable at the locations thereby providing for patient comfort during imaging. The head (28) contains an integrated assembly of the optical and mechanical components of the microscope. The assembly includes a main chassis plate (82). The optical components are mounted principally on one side of the plate while a PC board (130) is mounted on the opposite side of the plate. The board (130) mounts the electronic components, including interfaces, a microprocessor (222), and drivers (206, 208, 210) for motors (105, 106, 108) which control scanning and may also control fine positioning of the locations being imaged. The head (28) is detachable from the arm for manual disposition which is useful when imaging, not only the skin but other tissues, especially for research in investigating living processes at the cellular level.

19 Claims, 15 Drawing Sheets

U.S. PATENT DOCUMENTS

| | | | |
|---|---|---|---|
| 6,263,233 B1 | 7/2001 | Zavislan et al. | |
| 6,433,814 B1 | 8/2002 | Engelhardt | |
| 6,434,416 B1 * | 8/2002 | Mizoguchi et al. | 600/427 |
| 6,444,971 B1 * | 9/2002 | Engelhardt et al. | 250/214 DC |
| 6,648,478 B2 * | 11/2003 | Blank | 359/604 |
| 2003/0133840 A1 * | 7/2003 | Coombs et al. | 422/82.05 |
| 2005/0270639 A1 * | 12/2005 | Miki | 359/381 |

FOREIGN PATENT DOCUMENTS

| | | |
|---|---|---|
| DE | 196 54 207 A 1 | 6/1998 |
| EP | 0293228 | 11/1988 |

OTHER PUBLICATIONS

Rajadhyaksha, M. et al., In Vivo Confocal Scanning Laser Microscopy of Human Skin II: Advances in Instrumentation and Comparison With Histology, Journal of Investigative Dermatology, vol. 113, No. 3, pp. 293-303, 1999.

4 Digital Pictures showing different views of Internal Components of Confocal Microscope VIVASCOPE 1000, Manufactured by Lucid, Inc, prior to May 20, 2003.

* cited by examiner

US 7,859,749 B2

CONFOCAL MICROSCOPE FOR IMAGING OF SELECTED LOCATIONS OF THE BODY OF A PATIENT

This application is a Divisional of U.S. patent application Ser. No. 10/557,461, filed Nov. 18, 2005, now U.S. Pat No. 7,394,592 which claims priority to U.S. Provisional Application No. 60/471,911, filed 20 May 2003, which is herein incorporated by reference.

The present invention relates to confocal microscopes for the imaging of selected locations on the body of the patient and especially for the cellular imaging of skin at such locations as well as for the imaging of other living tissue and biological processes. The present invention provides a confocal microscope which is ergonometrically adapted to provide ease of use by containing the confocal microscope components, both optical and electronic, in an imaging head which is supported for precise placement of the confocal objective while eliminating the need for extensive re-orientation of the patient, thereby affording patient comfort during imaging.

It is a principal feature of the present invention to consolidate the optical and electronic components of a confocal microscope in compactly organized relationship, in an imaging head.

Another feature of the invention is to support the head on a positioning mechanism which provides for improved ergonomics in placing the head at precise locations against the skin of a patient without requiring the patient to be re-oriented in an uncomfortable position during imaging procedures.

It is a still further feature of the invention to support the confocal imaging head on an arm mechanism having a plurality of gimble connections providing freedom of displacement and rotation of the head so as to enable precise positioning thereof.

It is a still further feature of the invention to provide for the disconnection of the head for manual orientation which can facilitate imaging for research and clinical applications and investigation of cellular morphology and processes at the cellular level in skin and other tissues.

Confocal laser scanning microscopes have been provided, which have confocal imaging systems, suitable for imaging of skin and other cellular tissues, and reference may be had to Zavislan and Eastman, U.S. Pat. No. 5,788,639, issued Aug. 4, 1988, for Confocal Microscopes which may be hand held. Anderson et al., U.S. Pat. No. 5,880,880, issued Mar. 19, 1999 describes a confocal laser scanning microscope in which part of the optics are mounted in an arm. Such microscopes require electronic equipment for control and processing of image signals which are located separate and apart from the optics. While satisfactory images are obtainable with such laser scanning confocal microscopes, they have been difficult to use and may be ergonomically unsatisfactory to the clinician operating the microscope to obtain the images at selected positions on a patient.

The present invention provides a confocal microscope in which the optical and mechanical components are integrated and consolidated so as to provide an imaging head which is easy to position and has ergonomics which are desirable by clinicians. The head may be used without requiring the patient to be re-oriented with respect to the head in positions which may be uncomfortable for the patient.

Briefly described, a confocal microscope imaging head in accordance with the invention enables scanning of precise locations of the body of the patient and obtaining images of the skin and other tissue while consolidating the imaging and control electronics and the optical components of the microscope into a compact imaging head which is readily movable by the clinician. The head may have a main chassis plate, on opposite sides of which principal optical components of the microscope and electronic components may be mounted. The plate also supplies a support for the mechanism for fine positioning of the objective of the microscope, both in focus and laterally. The electronics of the head may be mounted on a printed circuit board attached adjacent to the chassis plate on one side thereof. The head may be mounted on a multi-axis compound arm having gimbals at joints between the arm segments, and where the arm is connected to an upright station on which a monitor (display) and a computer on which a keyboard for programming and operating the electronics of the head, may be mounted.

The foregoing and other features and advantages of the invention will become more apparent from a reading of the following description in connection with the accompanying drawings in which.

Figure 6:
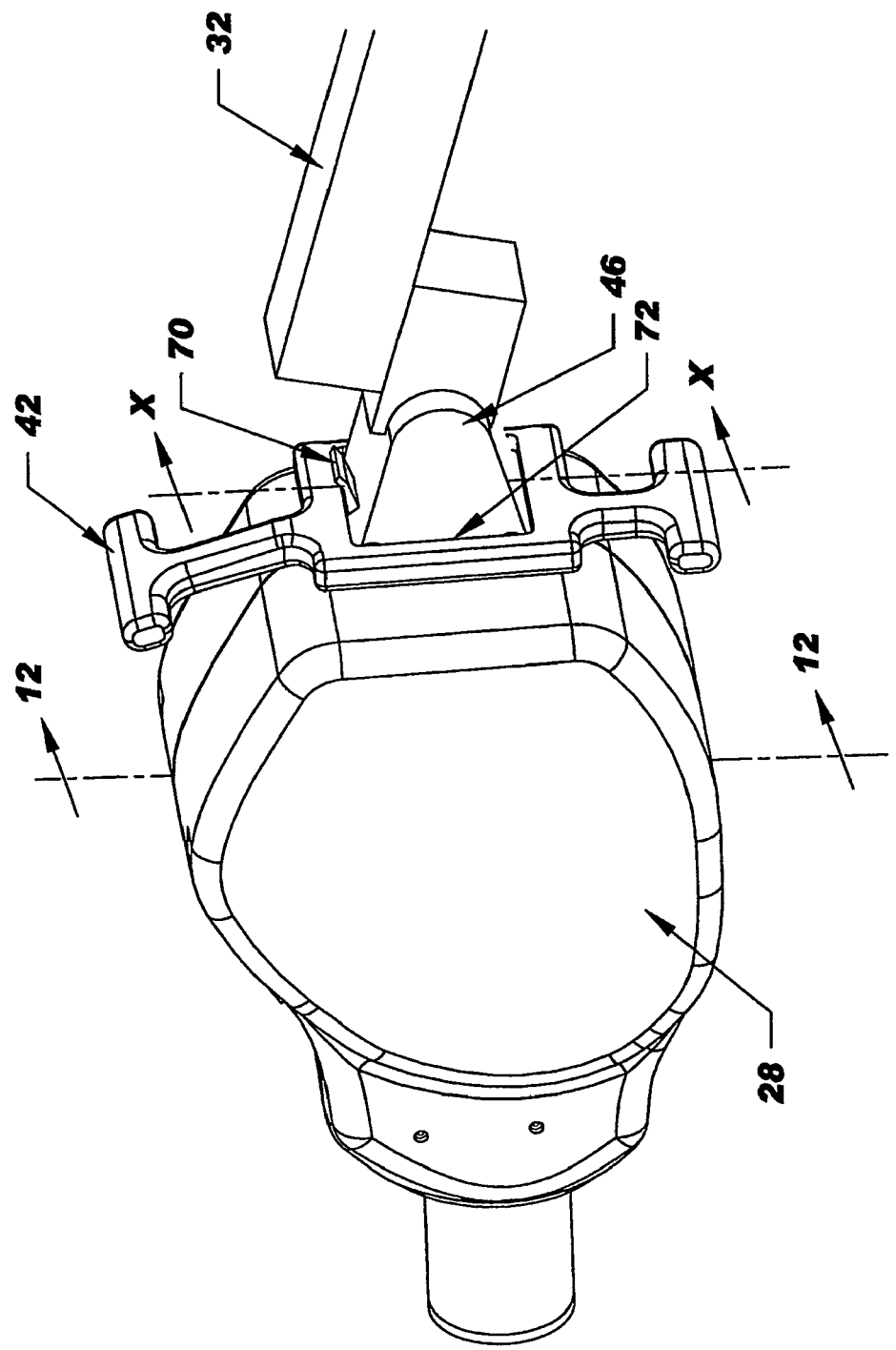
FIG. 6 is a perspective, side view of the head showing the head connected to the arm mechanism by a detachable connection.
Figure 7:
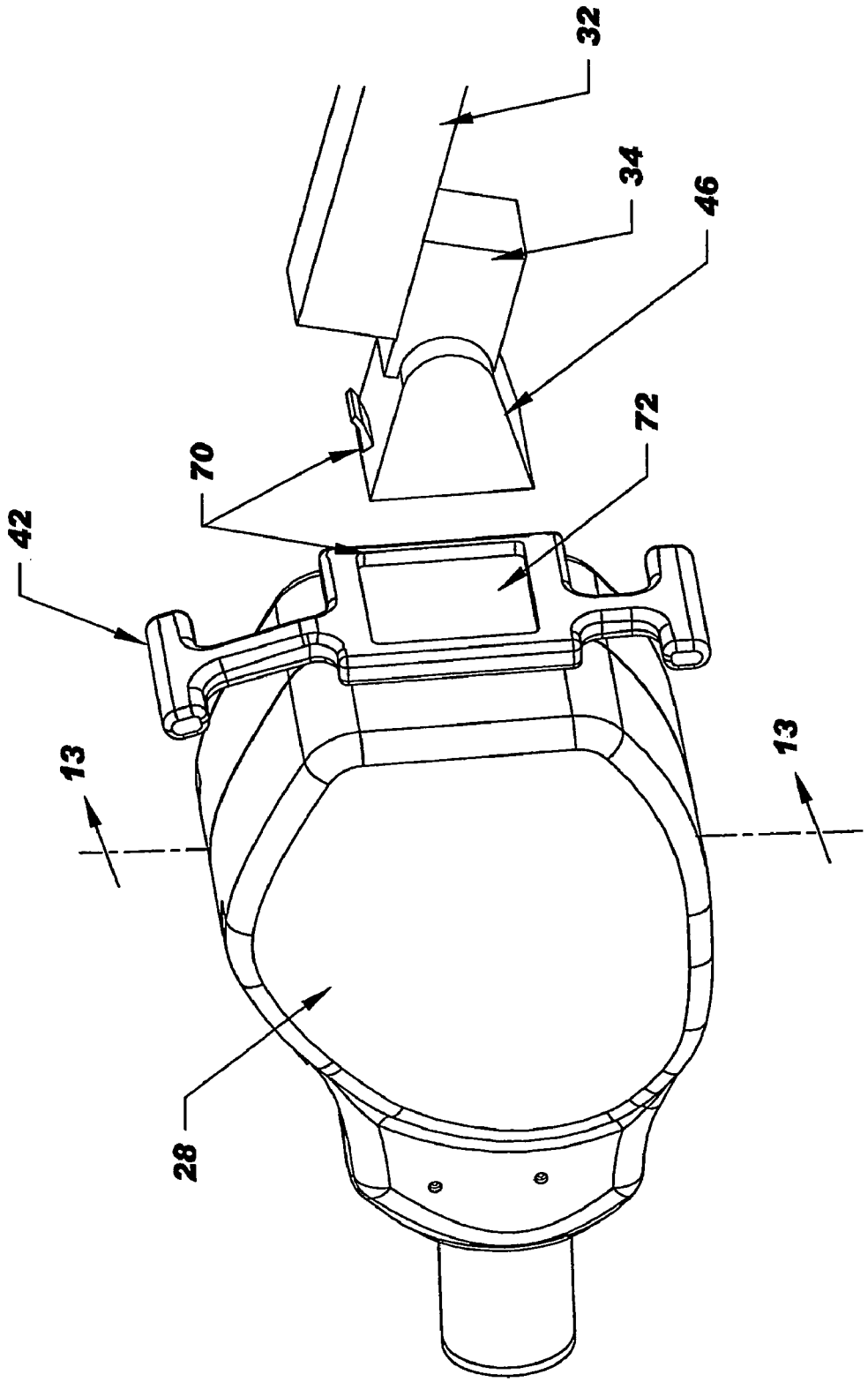
FIG. 7 is a view similar to FIG. 6 showing the head detached from the arm mechanism.
Figure 10:
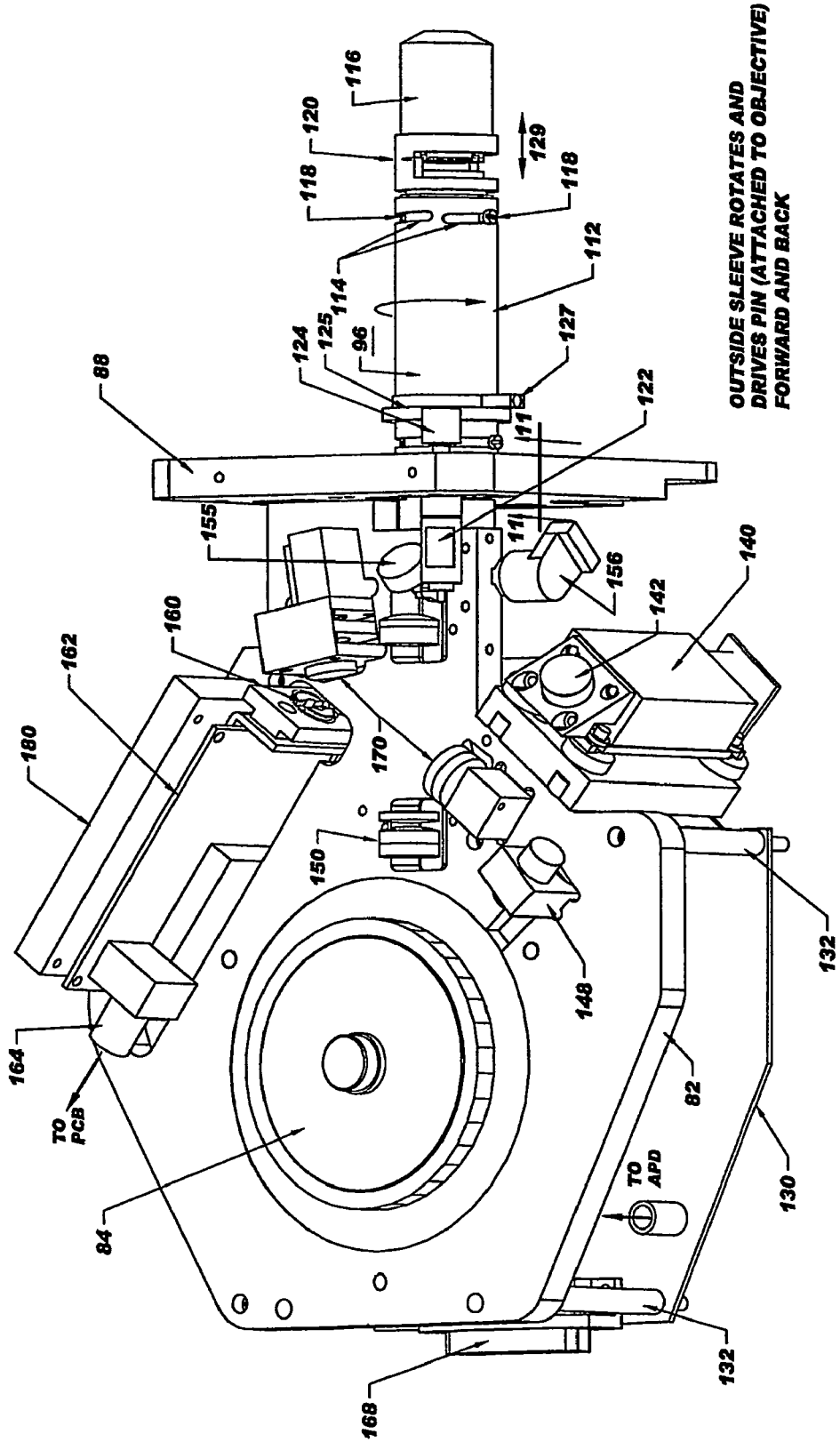
FIG. 10 is a perspective view illustrating the components of the imaging head including the objective lens and the mounting thereof to the chassis plate, from which the tubular nose structure surrounding the objective lens for fine positioning of the skin with respect to the objective omitted, to simplify the illustration.
Figure 11:
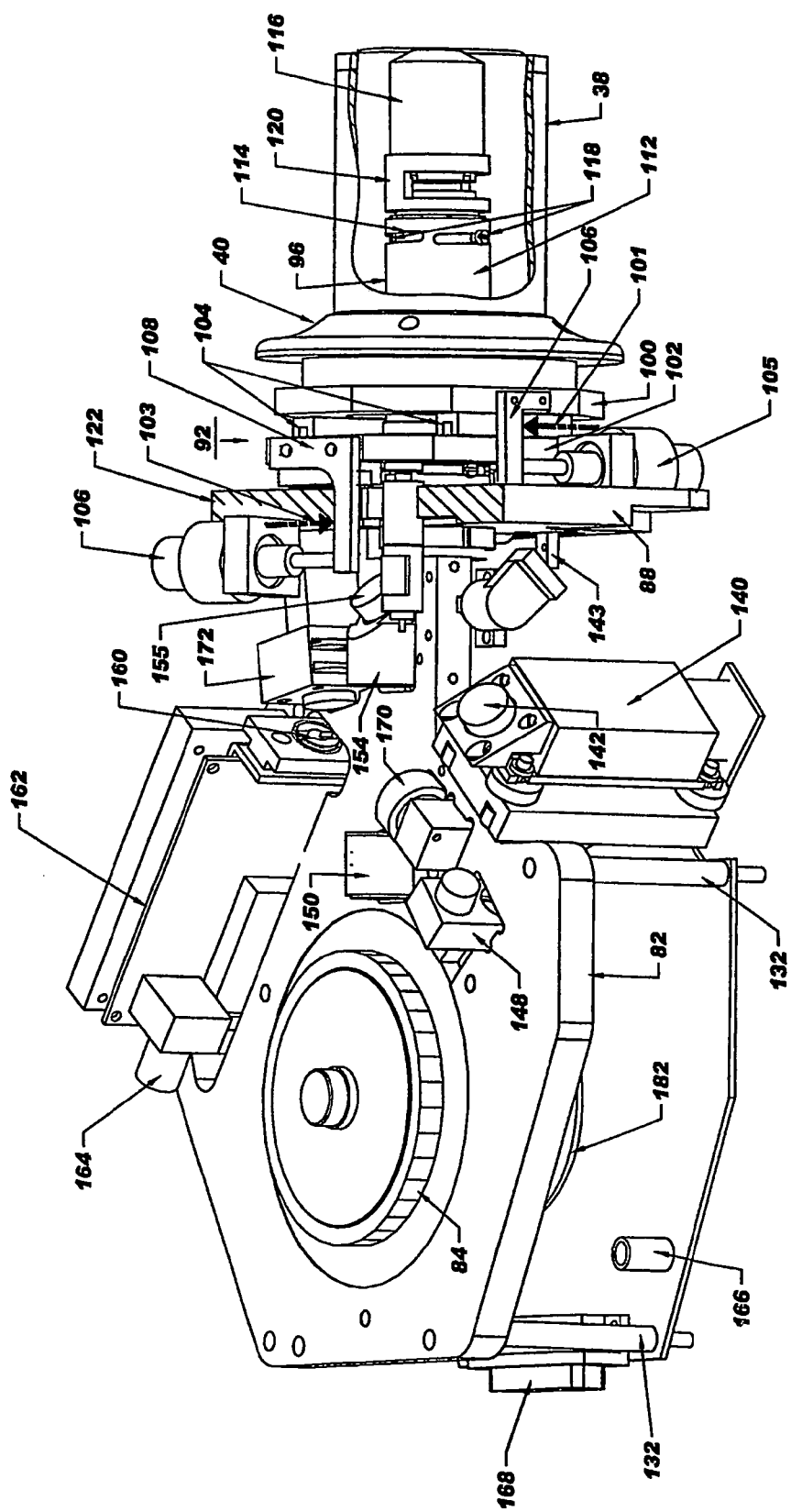
Figure 12:
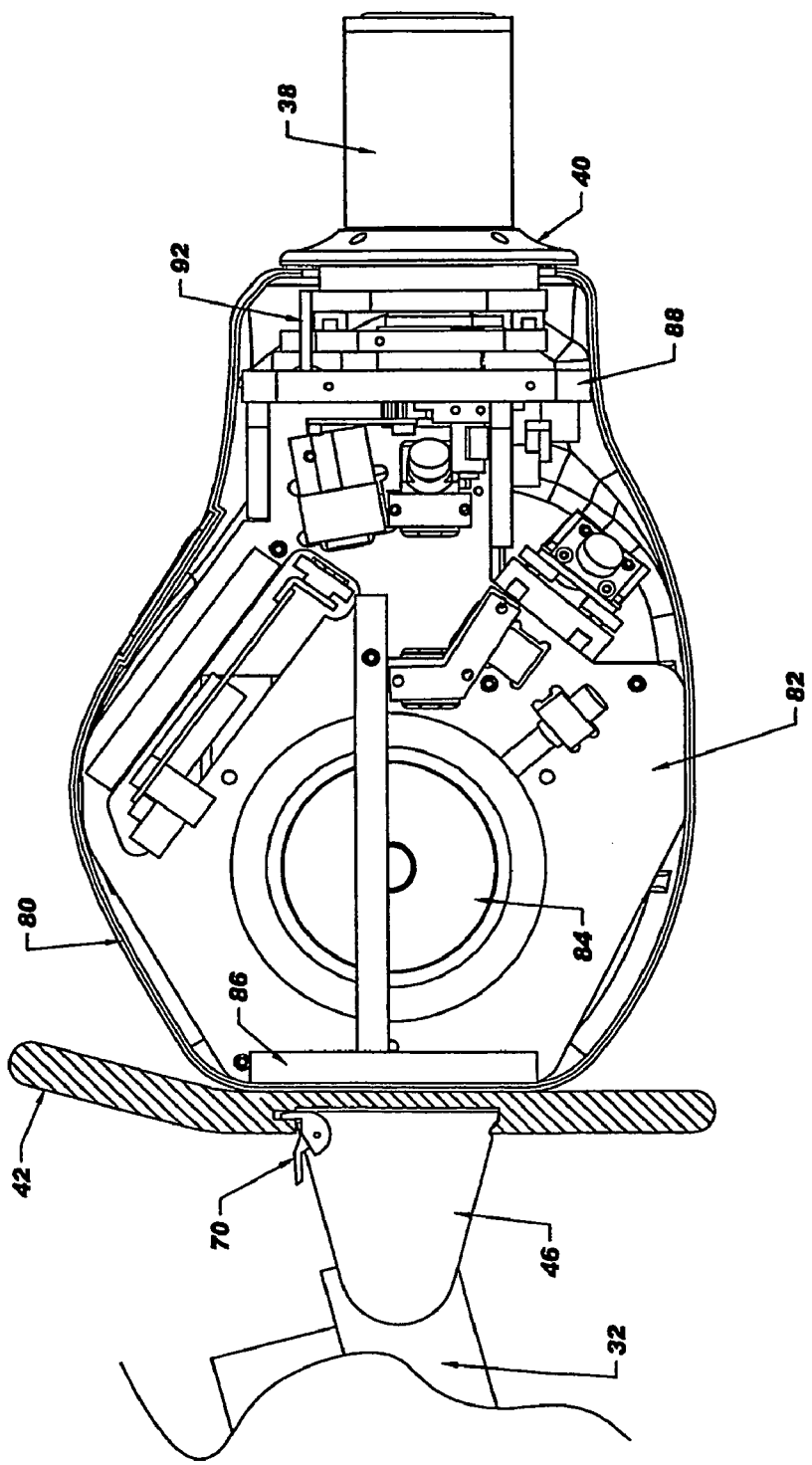
Figure 13:
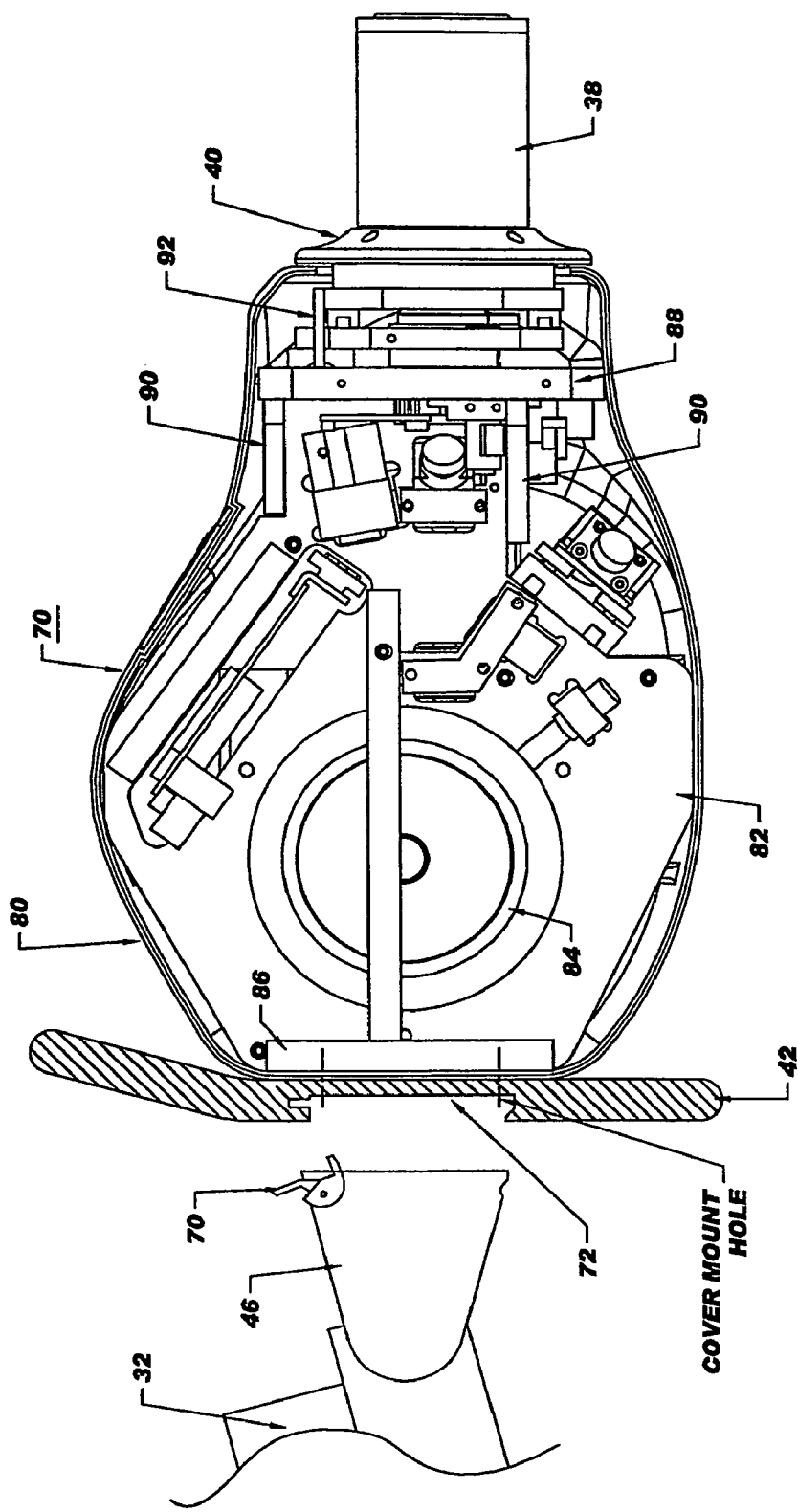

FIG. 11 is a perspective view similar to FIG. 10 but showing the tubular nose surrounding the objective lens and the stage for positioning the nose so as to locate the precise position of the skin being imaged, a portion of the mounting plate for the objective lens and the stage on which the nose is mounted being cut away along the line 11-11 in FIG. 10 to more clearly illustrate the mechanism for adjusting the stage and thereby adjusting the nose and precisely positioning the skin with respect to the objective;

FIG. 12 is a sectional view taken along the line 12-12 in FIG. 6;

FIG. 13 is a sectional view taken along the line 13-13 in FIG. 7; and

Figure 14:
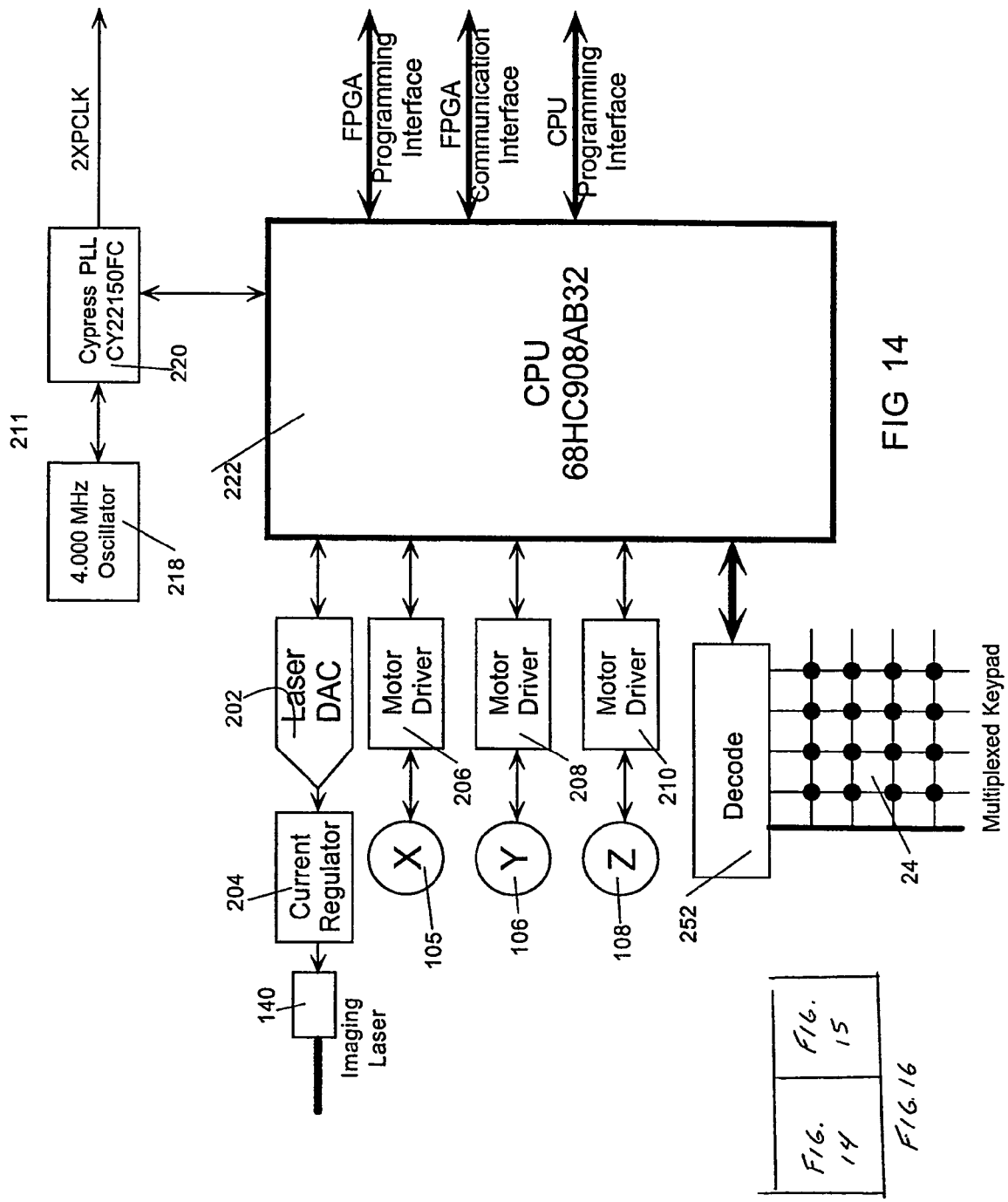
Figure 15:
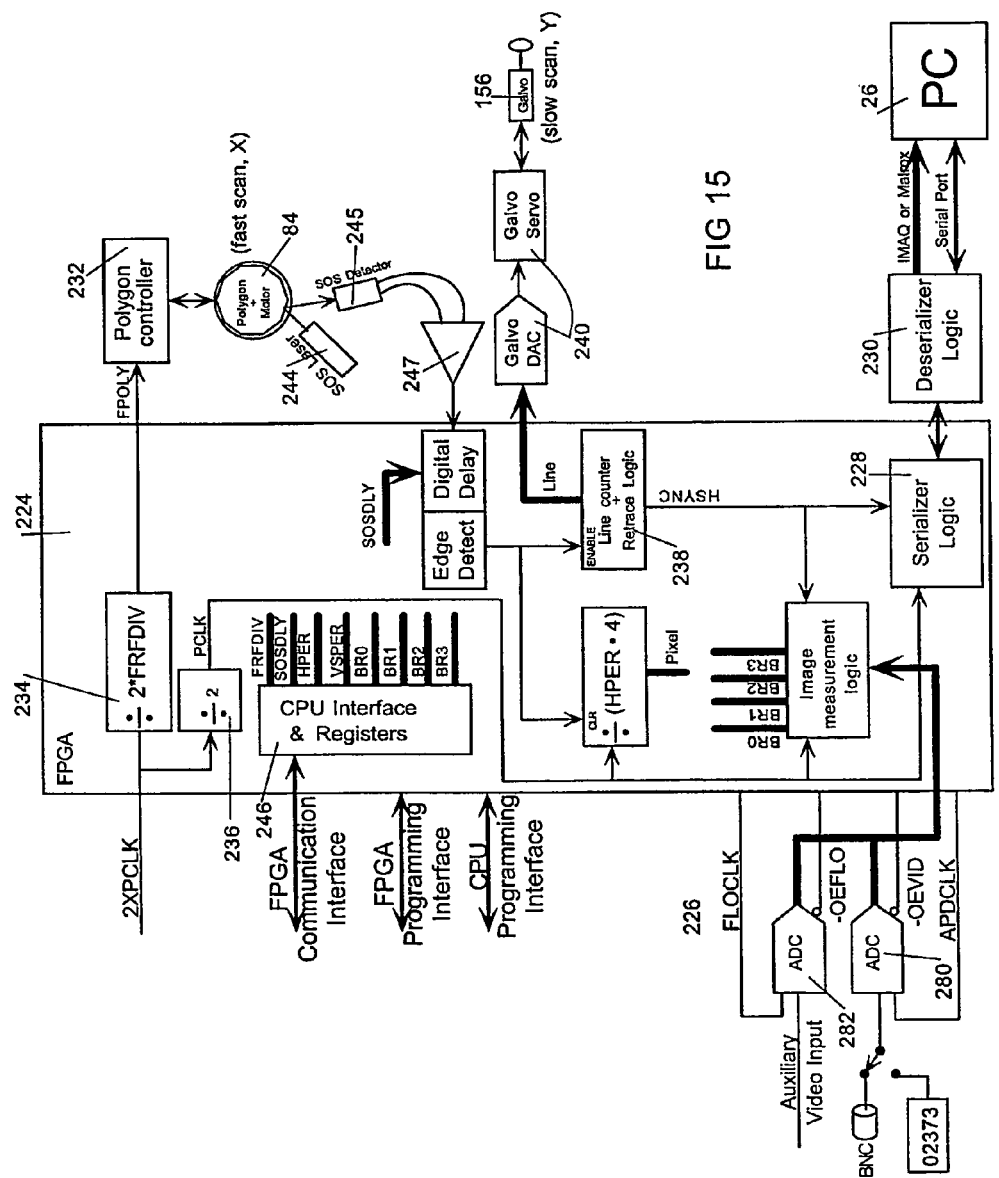

FIGS. 14 and 15 connected as shown in FIG. 16 is a block diagram of the electronics of the imaging head.

Figure 1:
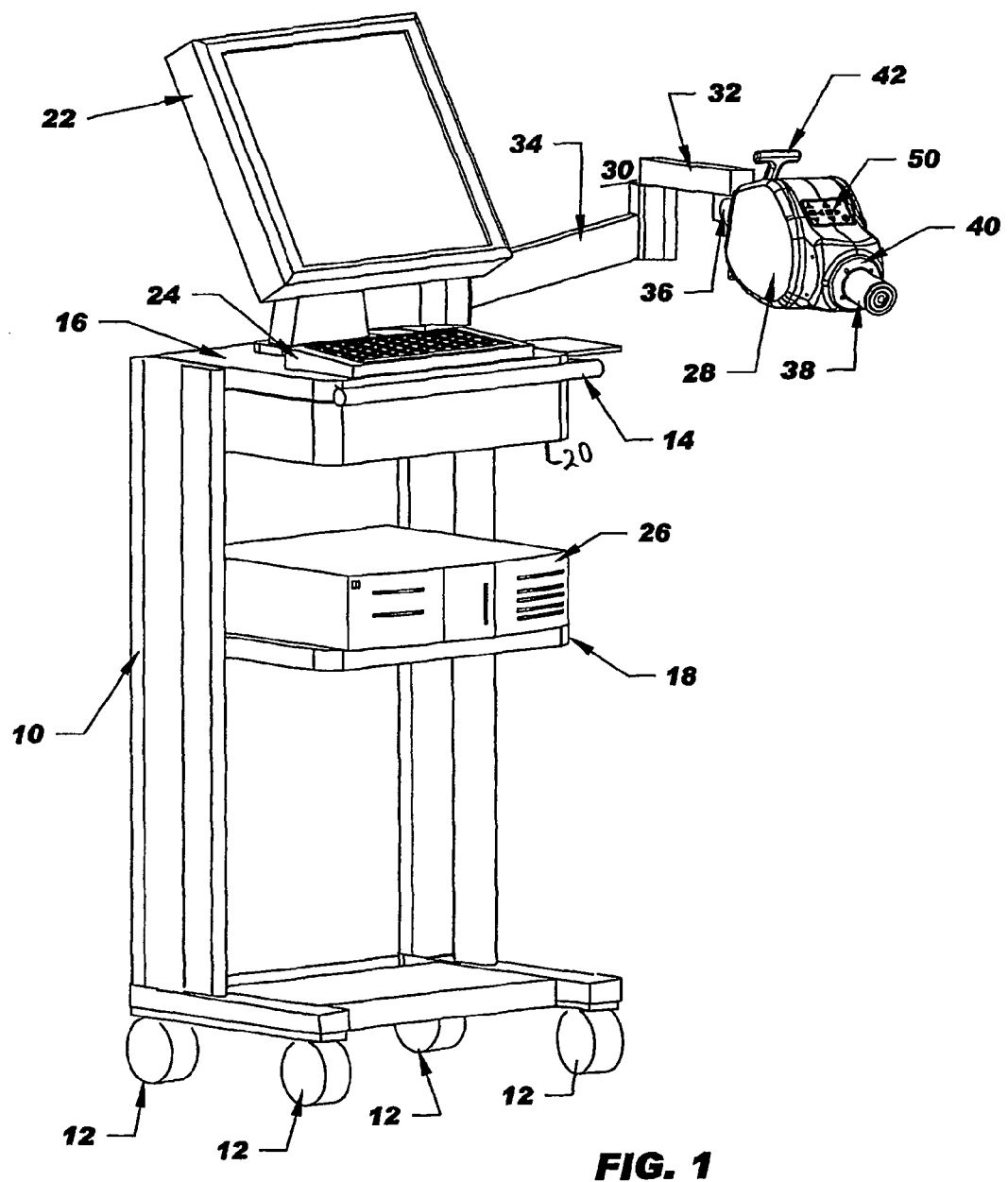
FIG. 1 is a perspective view of an improved laser scanning confocal microscope in accordance with the invention.
Figure 2:
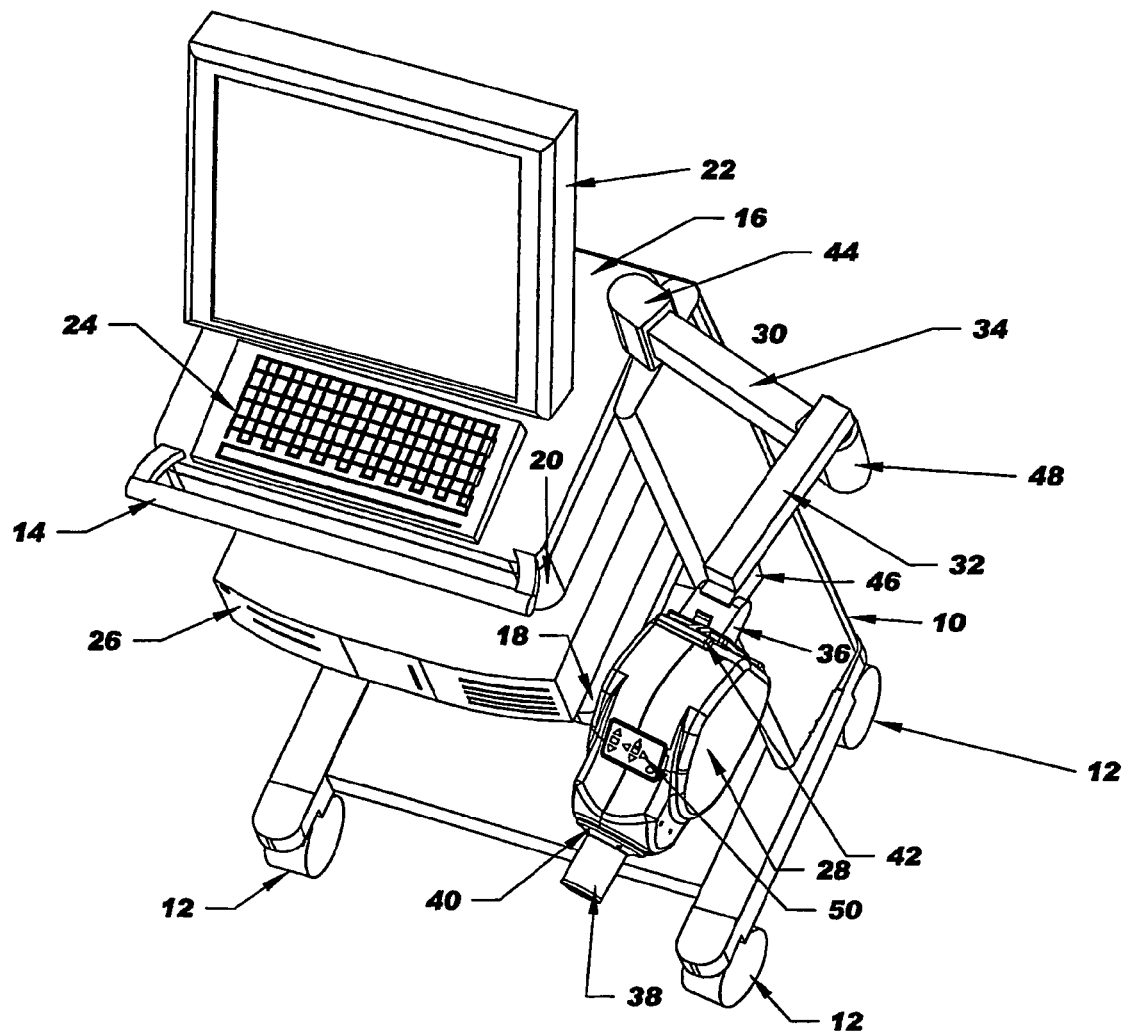
FIG. 2 is a perspective view of the microscope shown in FIG. 1 taken from the top.
Figure 3:
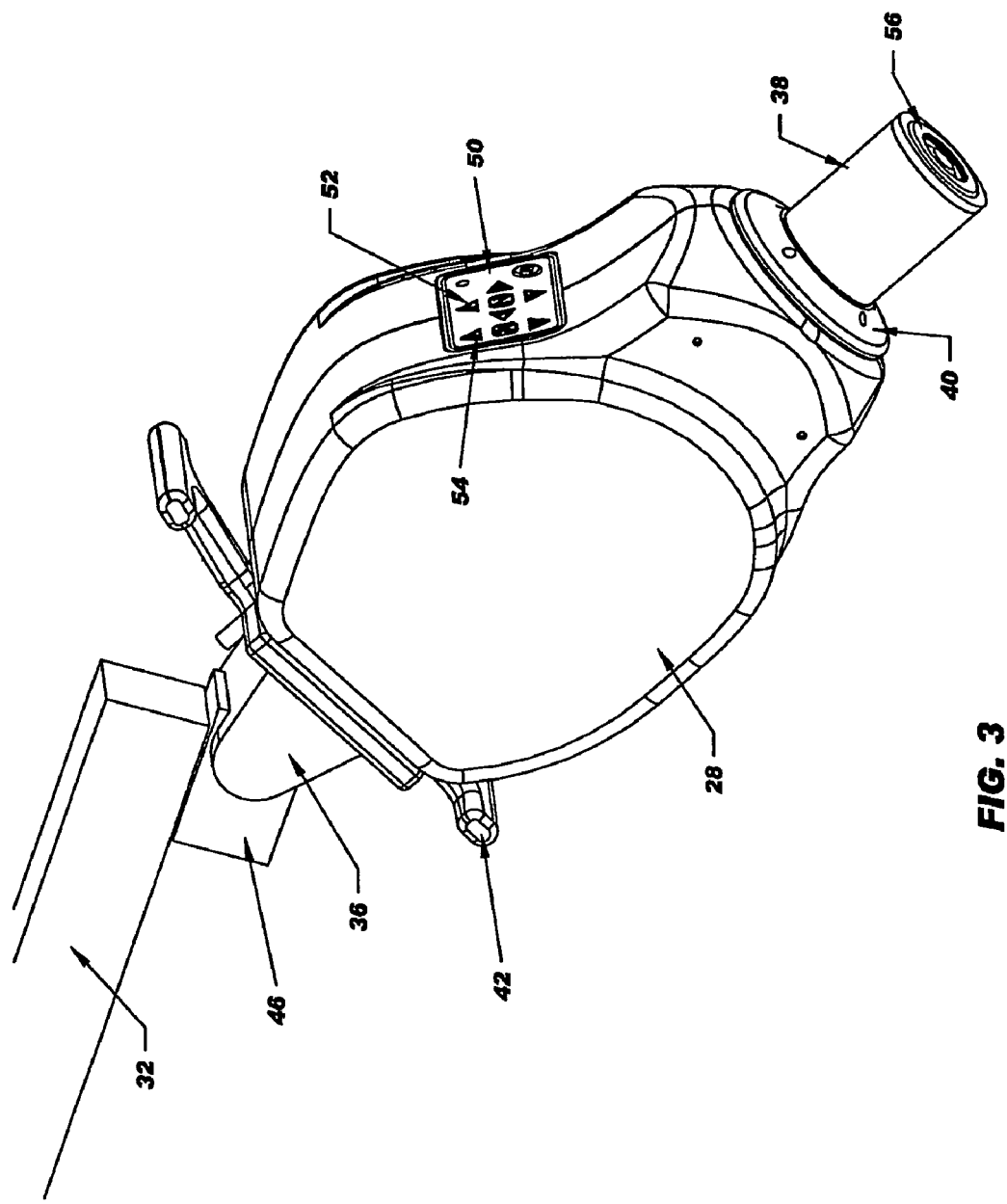
FIG. 3 is a perspective view of the imaging head attached to one part of a multi-axis displaceable and rotatable arm mechanism.

Referring more particularly to FIGS. 1, 2 and 3, there is shown an upright station 10 preferably mounted on casters 12 for movement along the floor as by manually gripping and pushing or pulling a bar 14. Shelves 16 and 18, one of which 16 may be above a drawer 20, are connected between uprights of the station 10. A flat panel monitor, and personal computer (PC) 26 may be placed on the lower shelf 18. The display 22 works with the computer 26 and also provides the images taken by the confocal microscope.

An imaging head 28 is gimble mounted on a multi-axis arm mechanism 30 having front and rear arms 32 and 34. The head 28 is removable at a coupling 36 on the free end of the front arm 32. The head 28 has a nose 38, preferably made of clear plastic, which is attached to a conical hub 40 on the front of the head 28. Handles 42 are manually grasped and moved to permit multi-axis movement of the head to bring the nose into contact with the skin of a patient or with other tissue to be imaged. The multi-axis movement is vertical, horizontal and rotational about gimble joints 44 and 46 at the rear end of the rear arm 34 and the front end of the front arm 32. A coupling joint 48 enables rotation of the arm 32 with respect to the arm 34. The multi-axis movement of the arms and the head 28 will be more apparent from FIGS. 4 and 5. There are cables from the head 28 to the PC 26 and between the PC, the monitor and the keyboard 24. These cables are not shown in the figures to simplify the illustration.

A control panel 50 on the side of the head 28 has two sets of controls 52 and 54. The controls 52 facilitate motion of the nose 38 in X and Y (orthogonal) directions so as to provide fine or precise positioning of the head with respect to the skin.

Control Panel Also has Provision for Capturing Images

In operation, the nose is brought into contact with the skin at the location to be imaged. The front end of the nose has a ring of removable double-sided adhesive material, the ring being in the circular area 56 at the front end of the nose. The nose is then moved in orthogonal directions and provides fine positioning, over distances much shorter than obtainable by manually moving the head through the use of the multi-axis, articulated arm mechanism 30. The location of the section on or internally of the skin location to be imaged is controllable by the controls 54, which cause the objective lens to move along the optical axis, out of and into the nose. Thus, the exact sections and the exact locations of the tissue of the body desired to be imaged is imaged.

Figure 4:
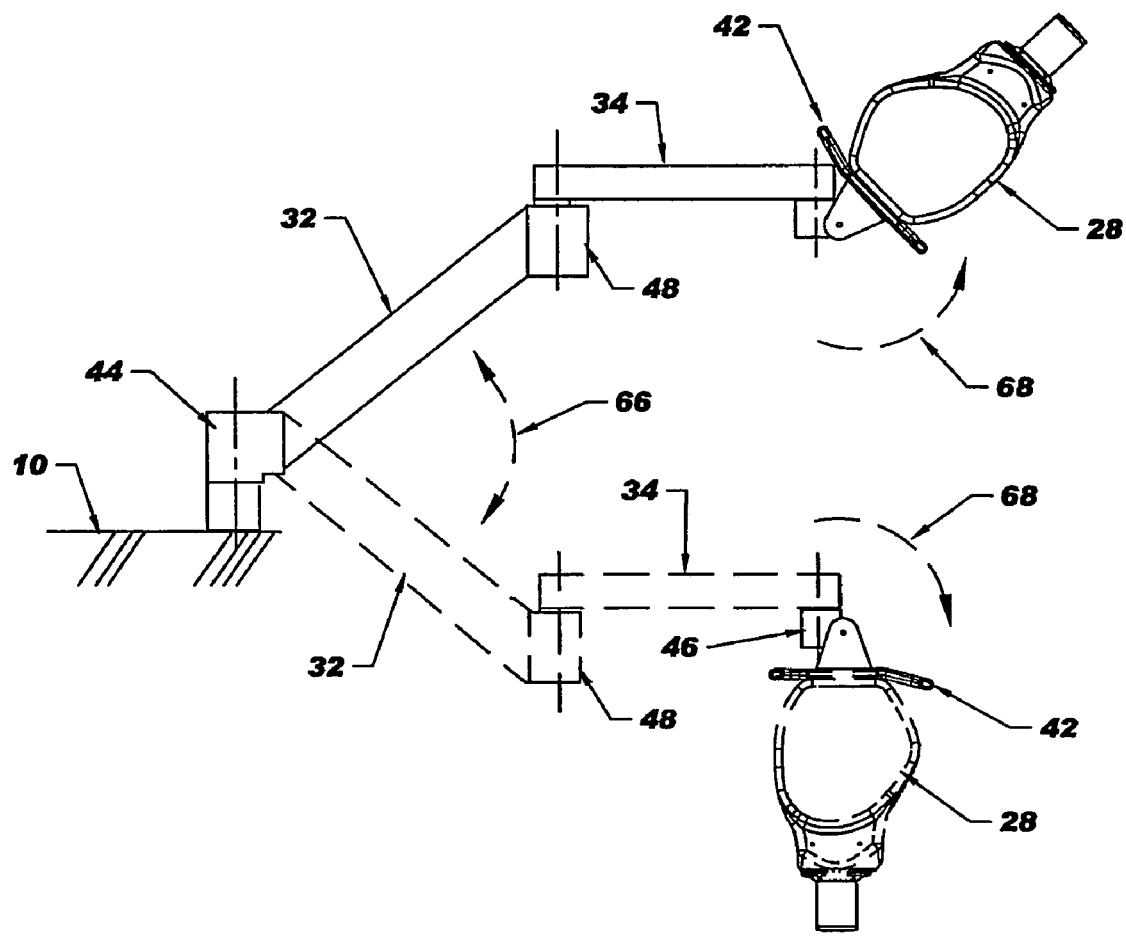
FIG. 4 is an elevational view illustrating the head and the multi-axis articulated arm mechanism showing positioning of the head both in displacement and in rotation.
Figure 5:
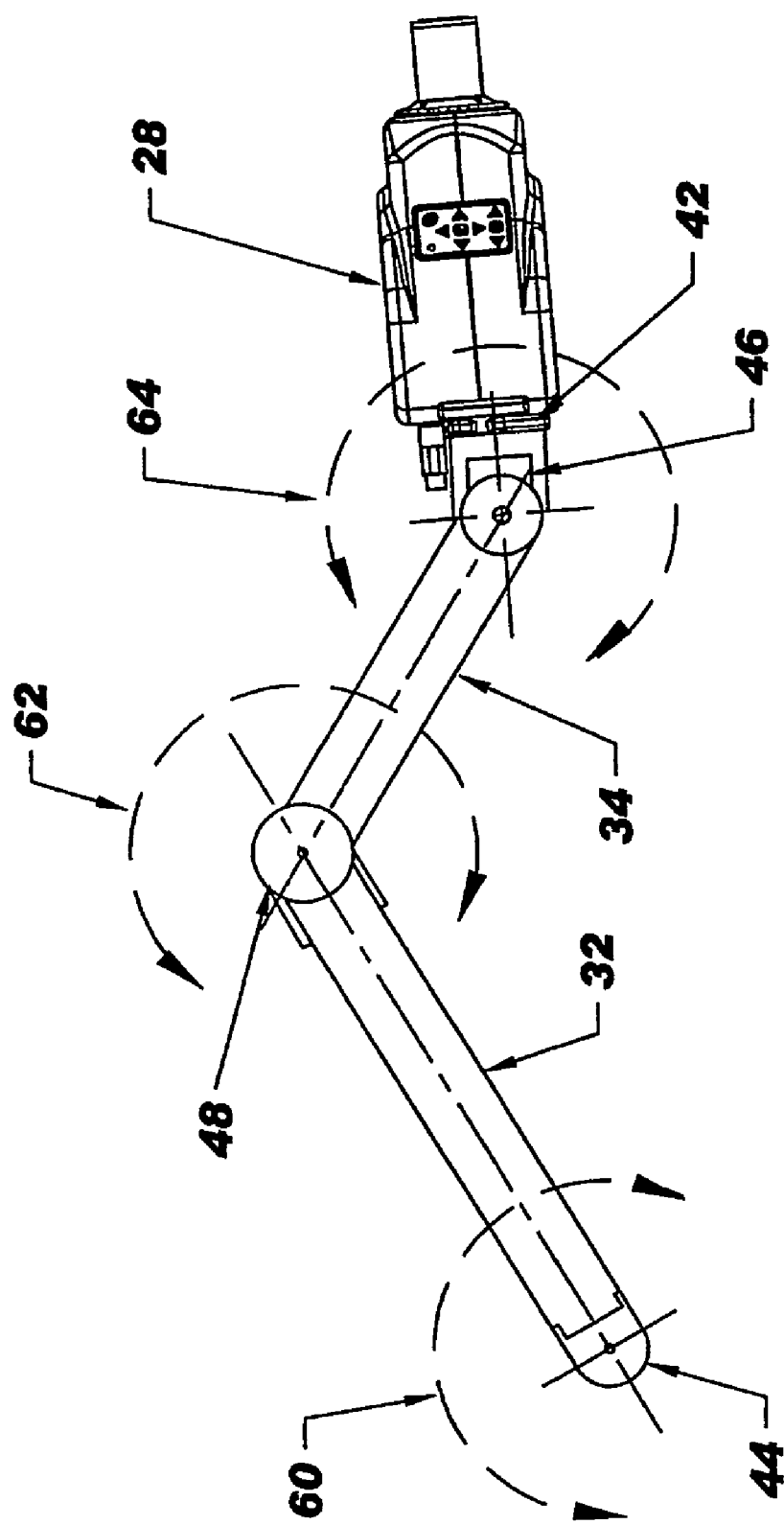
FIG. 5 is a plan view of the head and arm mechanism shown in FIG. 4.

The multi-axis movement of the head 28 will be more apparent from FIGS. 4 and 5. The gimble joints 44 and 46 enable rotational as well as vertical movement. The rotational movement is shown by arrows at the end of the dashed circle 60, 62 and 64 and the up and down movement or rotation about the gimbles 44 and 46 is shown by the arrows at the end of the dashed lines 66 and 68. The gimbles may be spring-loaded or have sufficient friction to enable the arms to stay in the position to which they are moved after the head 28 is located.

The detachability of the head 28 from the arms 30 may be obtained by a latch mechanism 70 in a receptacle 72 in the handle 42 (see also FIG. 6). When the latch 70 is released, the head 28 held by handles 42 may be moved and oriented manually, separately from the arm mechanism 30. This receptacle and mechanism is also illustrated in FIGS. 12 and 13.

FIGS. 12 and 13 also show the internals of the confocal microscope head and the bi-part case or housing 80. This case is connected to a main chassis plate 82. A T-shaped bracket which bridges a polygon scanner 84 and presents a rear support plate 86, which provides a firm and solid connection for the rear of the case 80 and for the handles to the head 28. A forward support plate 88, which is connected to the main chassis plate 82 by gussets 90, also has screw holes to which screws (not shown) are inserted so as to attach the parts of the case 80.

The plate 88 also supports an XY stage 92 to which the nose 38 and its mounting hub 40 are connected, and are movable via the stage 92 for fine positioning, laterally in X and Y directions.

As shown in FIGS. 10 and 11, an objective lens assembly 96 is also supported by the plate 88. The stage 92, as shown in FIG. 11, has forward and rear plates 100 and 102. Slides 104 allow the movement of the forward plate 100 in the Y direction shown by arrow 103, when actuated by the shaft of a linear stepper motor 105 via an arm 106. The rear plate 102 of the stage 92 is moveable in a direction perpendicular to the movement of the front plate 100. The rear plate 102 is mounted on slides (not shown) attached to the support forward plate 88. A linear stepper motor 106 has a shaft connected via an arm 108 to move the plate 102 and objective 38 in the X direction shown by arrow 103.

The objective lens assembly 96 includes an objective lens 116 in a lens barrel. A tube 112 has cam slots 114. Pins 118 in these slots are connected via a coupling 120 to the objective lens 116. When the tube 96 is rotated by a motor 122 via a pinion 124 and ring gear (not shown) around the periphery of the tube 96, the cam slots cause the pins to translate forward or backward, depending upon the direction of the rotation of the motor 122, thereby moving the objective 116 forward and backwards along its optical axis so as to focus the objective at the section of the tissue to be imaged.

A barrel inside of the rotating tube 112 contains a pair of compound lenses 131 and 132 forms part of a forward telescope lens 134. The forward telescope 134 is assembled inside the rotatable tube 112 of the objective lens focusing mechanism. The later mechanism is shown in FIGS. 10 and 11. A finger 127 on the rotating tube 112 may be used in conjunction with an opto photosensor (not shown) to indicate to the electronics the location in the direction of the arrows 129 (FIG. 10) of the objective 116.

Figure 8:
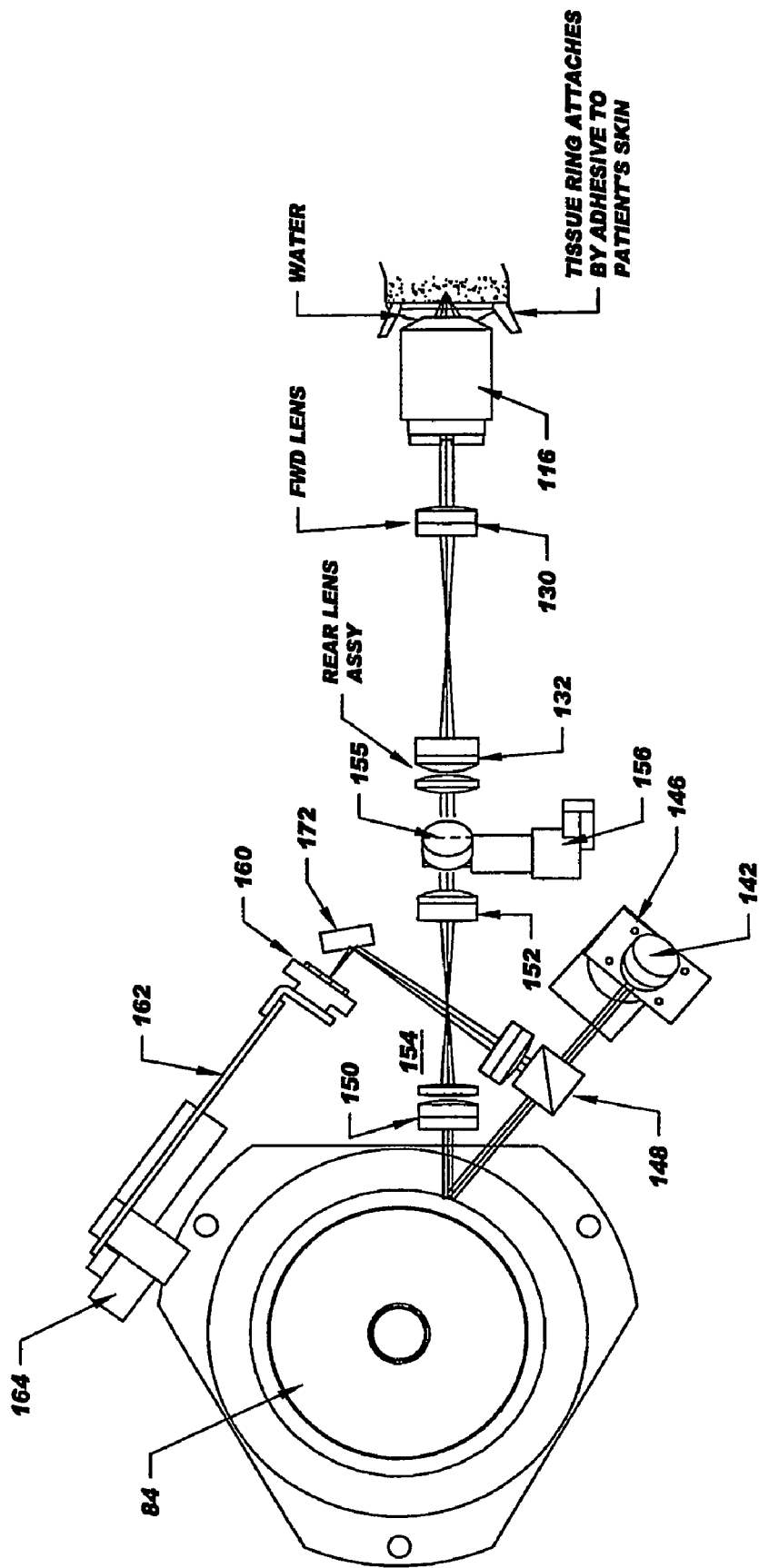
FIG. 8 is a plan view illustrating the ray paths of the beams in the head of the confocal microscope shown in the preceding figures.
Figure 9:
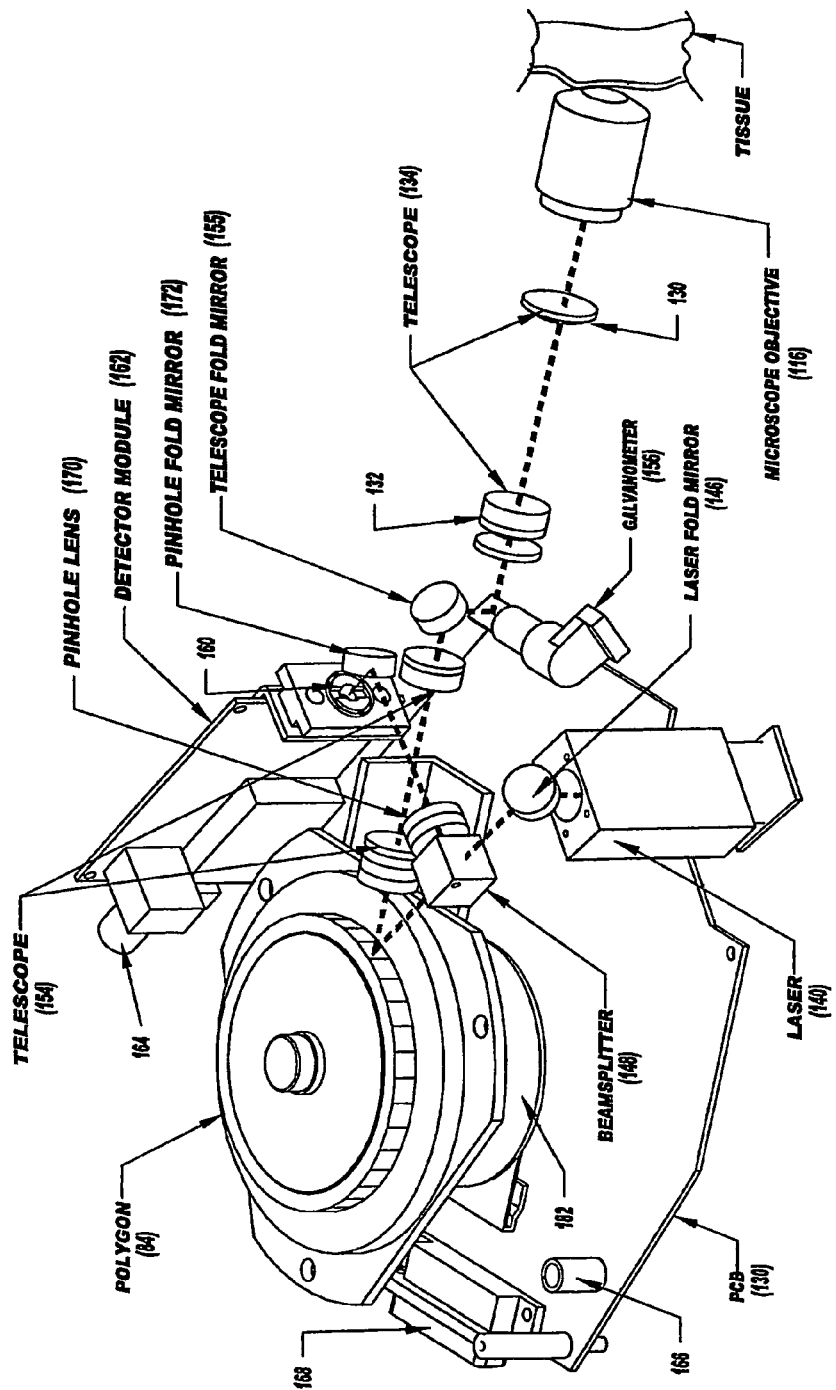
FIG. 9 is a simplified perspective view showing the optical components and PCB for mounting the electronic components, with the mounting chassis plate removed so as to more clearly illustrate the PCB and the optical components.

FIG. 8 shows the optical components of the confocal microscope head 28. It will be apparent from FIG. 8 and FIG. 9 and also from the location of these components in FIGS. 10 and 11 that the components are principally on the upper side of the mounting plate 82 and their connected thereto. FIGS. 9, 10 and 11 also show a printed circuit board (PCB) 130 which is attached in parallel spaced relationship to the underside of the mounting plate 82; the spacing being afforded by spacers 132. Substantially all of the electronic components are mounted on the PCB 130. These components will be discussed in connection with the circuit diagram (FIGS. 14 and 15).

The optical components of the confocal microscope are the compound lenses 131 and 132 of the telescope 134, the objective 116 and the polygon 84 which have already be mentioned. The other components are a laser 140 having a folding mirror 142. A beam splitter 148 is in the path of the light to the reflecting facets of the polygon 84. The polygon may have a multiplicity (say 36) facets. The facets provide successive scan lines of the image being formed.

Two compound lenses 150 and 152 form a second telescope which confines the beam and is bent in a telescope fold mirror. A galvanometer 156 deflects the beam in a cross scan direction so as to displace the scan lines of the image. The beam then passes through the telescope 134 and the objective 116. The beam is focused by the objective lens and then reflected from the section of the tissue (patients body location), being imaged, back through the objective 116, the telescope 134, the galvanometer 156 mirror, the fold mirror 155, the second telescope 154 and the polygon facet, then de-scanning the line, to the beam splitter 148. The beam splitter 148 directs the beam to a confocal pinhole aperture 160 of a pinhole detector assembly 162. This assembly includes the detector which may be an avalanche photodiode and electronics mounted on a board for developing a video signal corresponding to the image. This video signal is carried by a cable not shown via connectors 164 and 166 on the detector modular 162 and the PC board 130 for processing via electronics on the board 130 into an image-forming signal. This signal is carried by a connector 168 on the PCB 130 via a cable (not shown) to the PC for providing the image on the display 22. The signal may be transmitted for telepathological observation at remote points or the image printed using a high-resolution (megapixel) printer.

The return beam from the beam splitter 148 is focused on the pinhole aperture 160 by a pinhole lens 170 and a fold mirror 172.

It is the feature of the invention to provide compactness optics as well as location thereof in essentially the same plane on the upper surface of the main chassis support plate. This end is obtained by the arrangement of the optical components so that the beam in the part of the optical path between galvanometer and the polygon 84 (principally in the confines of the second telescope lens 154) crosses the beam in the return path from the beam splitter 148 to the pinhole aperture 160. The beam portions cross at an angle which exceeds a minimum angle, thereby avoiding any significant interference of the light in the crossing beams. It will be noted that all the optical components are mounted on the main chassis plate 82 and almost all are mounted on the upper surface of that plate.

The photo detector 162 includes a bar 180 which mounts the photo detector on the upper surface of the plate 82. The galvanometer is mounted on a bracket 143 attached to the front support plate 88, so that galvanometer-reflecting mirror is in the plane of the optical rays above the upper surface of the main chassis plate 88. The polygon 84 is above the plate 88. The polygon drive shaft (not shown) for rotating the polygon 84 extends through the plate 82. A drive motor 182 connected to the polygon drive shaft may be mounted on the PCB 130.

The circuits on the PCB 130 comprise an imaging laser driver circuit 145 for powering the laser 140. This driver circuit includes a laser digital to analog converter (DAC) 202, and a laser current regulator 204. There are three stepper motor drivers 206, 208, and 210 which drive the X direction stage drive motor 105, the Y direction stage drive motor 106 and the motor 108 which moves the objective lens 116 in the Z direction. There are pixel clock generator circuits 211 including an oscillator 218 and a phase lock loop (PLL) frequency synthesizer circuit 220. A microprocessor CPU 222 on the board 130 is connected to the DAC 202, and to drivers 206, 208, and 210. The CPU 222 is connected via interface lines to a field programmable gate array (FPGA) integrated circuit 224. There are image data handling circuits 226, as well as synchronization serializer logic 228 which primarily reduces the number of physical connections between the imaging head 28 and PC 26 so as to allow use of a non-bulky cable between the two. The deserializer logic 230 also handles image formatting in the PC. The polygon motor 84 is speed regulated by a polygon controller circuit 232 which receives a reference speed signal, in the form of a frequency, from pixel clock through programmable divider 234 on the FPGA. The serializer logic also receives the pixel clock through a divider 236 for transmission to PC 26 for image recovery. Image formation is provided by scanning the outgoing laser beam onto the tissue sample in raster fashion. The fast axis is produced by rotating polygon 84 and the slow axis by galvanometer 156. The reflectance properties of the tissue are measured by converting the refracted light, as conditioned by the optics, described on subsequent pages, to a time-varying electronic signal voltage by photodetector 162. This signal is converted to a digital value by analog to digital converter 280. A synchronous circuit including line counter and retrace logic 238 drives a galvanometer controller including a digital to analog converter 240. A galvanometer servo 242 is connected to the galvanometer 156. The polygon position is detected by a polygon position (start of scan—SOS) detector that produces a digital pulse as each consecutive polygon facet scans the outgoing laser beam across the tissue sample. Line counter and retrace logic 238 counts these SOS edges to control the position of galvanometer 156. Digital to analog circuit 240 converts the line counter value to an analog voltage that ultimately controls galvo 156's angular position. There is a circuit (not shown) for activating the monitor 22, there are also register circuits 246 on the FPGA interface that allow the CPU 222 to programming the various FPGA scanning parameters.

The CPU 222 also receives commands from the head control keyboard 24 on the casing of the imaging head 28 via a firmware decoder 252 so as to operate the X, Y and Z motors, 104, 106, and 108, via their drivers.

During operation, firmware directs the microprocessor, using the FPGA 224 implemented serializer/deserializer interface 241, to accept commands from the host PC via its serial (RS-232) port and from the on-board keypad 24. These commands direct the on-board microprocessor 222 to initiate scanning, control laser current, stepper motor positions, polygon rotational. Programmable divider 234 provides control of the polygon reference frequency, FPOLY, independently of pixel clock. In doing so, establishes the image's width, in pixels. Likewise, the HPER and VSPER inputs to line counter block 238 establish the displayed image's height.

In addition to the above-mentioned functions, the microprocessor 222 periodically scans its keyboard to detect control activations. Several front panel keys have predefined functions that include: starting and stopping imaging (scanning) mode, moving each of three stepper motors, controlling laser operating current (and thereby laser operating power), image capture, image stacking, stacking or sectional imaging as determined by which function is currently active. An addition button can be included to select the active imaging function. This feature can also be incorporated into the PC's application program. A brief description of each key function follows.

The command structure allows the host PC to override local controls, and/or obtain the states of local controls at its discretion.

Scan/Stop Scan

A scan/stop scan button directs the microprocessor 222 to initiate or discontinue scanning (depending on the current state of scanning), by performing several related tasks. These tasks consist of programming the pixel clock generating PLL 220 and various FPGA registers 246 (see Microprocessor/FPGA interface) according to predefined imaging parameters (such as image width, height and, frame rate), and setting the laser current DAC to an initial value.

Laser Current Control

As described in subsequent sections, imaging laser power is indirectly controlled by laser operating current see (imaging laser driver).

Presses of the increase laser current control cause the microprocessor to increase the laser DAC 202 setting, whereas presses of the decrease laser current control cause the microprocessor 222 to decrease the laser DAC setting.

Laser current is set to its minimum value during non-scanning periods by the microprocessor.

X, Y, Z Motor Movement

Three stage positioning stepper motors control imaging depth (Z), and specimen position (X, Y). These stepper motors 104, 106, 108 are controlled by the microprocessor in response to motor movement controls: X+, X−, Y+, Y−, Z+, and Z−. Both fine and course movement modes are available that move one step per key activation and multiple steps per key activation according to the current movement mode (fine or coarse), respectively.

Fine/Coarse Mode Selection

The fine/coarse mode control alternately selects Fine or Coarse movement mode. Microprocessor firmware implements these modes by issuing either one, or multiple step commands to the associated motor when its associated motor movement control is activated, respectively.

Image Function Selection

There are three imaging modes: image capture, VivaStack® and VivaBlock®. Image capture is simply capturing a single frame from the live video feed. Sectioning is a series of images, taken at various predefined depths at the same X, Y location. Stacking is a series of images, taken at the same depth, that are stitched together to form a large area image.

The image mode control alternately select between these modes. This control's state is relayed to the PC application program for processing. It is the PC 26 application program that implements and organizes these functions.

Imaging Laser Driver

The imaging laser 140 is operated in constant current mode. In this mode, laser power is virtually constant. There is a slight temperature influence on laser power, however, the thermal mass of the laser is large and the internal operating temperature is fairly constant, thus actual operating power changes are small, typically only 1 or 2%. thus maintaining virtually constant target signal reflectance (e.g. image brightness).

Laser current is regulated by a constant-current load type circuit 204. The constant current load circuit is driven by the DAC 202 whose output is controlled by the on-board microprocessor 222.

Stepper Motor Drivers

Three PWM mode current regulated motor drivers provide three axis motion, X, Y and focal depth, Z, for the specimen stage 92. The on-board microprocessor 222 in response to front-panel controls 24, positions these stages allowing direct operator control of specimen position.

The motor supply voltage is chosen to be considerably higher than the motor ratings so as to produce current slew-rates that are significantly higher than they would otherwise be, providing improved step response. The driver circuits 206, 208 and 210 regulate motor current insuring the motors don't overheat. Several current levels are selectable by the microprocessor allowing the motors to operate at lower current levels to maintain position at reduced motor power dissipation levels.

Keyboard Multiplexer

The keyboard 24 activates key features and operating modes as well as controls motor positions and imaging laser power (via its operating current). Keyboard status is multiplexed through a serial interface to the control application program running on the PC 26.

The keyboard 24 is a standard 4×4 row-column multiplexed design and is controlled by the on-board microprocessor 222 to allow easy key code assignment. Decoder 252 is firmware implemented with minimal external circuitry provided to accomplish this function.

Pixel Clock Generating PLL

A programmable phase-locked loop frequency synthesizer generates pixel clock (a clock used to sample the imaging digitizer(s) one cycle per pixel). The PLL can generate accurate and stable clock frequencies from 5 to 100 MHz.

The PLL 220 is programmed by the microprocessor 222 to generate the appropriate clock frequency based on operator specified image parameters (e.g. width and height).

Dual Imaging Digitizers

In the video image signal digitizer 220, there are two high-speed 10-bit A/D converters 280 and 282 to convert analog reflectance signals from up to two analog signal sources. The first source is the normal reflectance channel that is proportional to the instantaneous target reflectance and laser power product. The second detector channel may be sensitive to a secondary illuminating light wavelength, or light property such as fluorescence.

The digital reflectance data is processed within the FPGA 227 and multiplexed into the outgoing data stream for subsequent display or further processing by the PC.

Microprocessor/FPGA Interface

Several functions are implemented within the FPGA 227. Due to its programmable nature, the FPGA can be reconfigured to implement additional operations.

The microprocessor interfaces to the FPGA with a conventional parallel data bus. The FPGA is organized as a series of eight, 8-bit control registers 246 that are directly accessible by the microprocessor 222. Three address signals from the microprocessor select which FPGA register is to be accessed. Two additional control signals, R_/W and XFR complete the interface. The level of R_/W controls transfer direction (e.g. data bus direction) and XFR acts as a data transfer strobe. This interface can be expanded almost indefinitely by defining register selection bits within the FPGA logic. That is to say, define a register whose value selects access to an alternate set(s) of registers.

Imaging Data & Synchronization Serializer Logic

The serializer reduces signal connections between imaginghead 28 and the PC 26 thereby eliminating the need for bulky cables. The parallel data signals as well as horizontal and vertical synchronization cycles are time-division multiplexed. Two data recovery clock signals complete the interface and allow for easy and reliable signal extraction by the deserializer 230. Numerous data signals can expand the interface bandwidth as desired at of course the expense of the number of cable conductors.

The deserializer circuitry 230 may be housed in the PC 26 and converts the serialized data and control signals back to their original form for presentation to the video capture board and serial port interfaces in the PC.

Brushless DC Motor Controller

The rotating polygon 84 implements the high-speed (horizontal) scanning axis. The outgoing laser beam is swept across the specimen in the horizontal direction by the moving facets.

The polygon motor may be a three-phase, 120°, brushless DC motor. A current regulating, PWM switched control IC provides basic phase commutation and current regulation. This IC is part of a secondary speed regulating circuit.

A reference frequency, called $F_{POLY}$, produced within the FPGA (derived from pixel clock), establishes the basic rotational speed for the polygon motor, and thus the line scan frequency. Since this frequency is dependent upon pixel clock (which controls sampling), the ratio of these frequencies controls image width. The polygon speed controller is a closed-loop feedback servo that acts to regulate motor speed by comparing the frequency of one hall-effect sensor phase (whose output is two cycles per motor revolution), with a reference frequency named $F_{poly}$. The frequencies are converted within the speed controller circuitry to DC, ground-referenced voltages that are proportional to motor speed. These voltages are inputs to a traditional analog subtracter. The subtracter output is applied to the current input control of the PWM switched control IC mentioned above, thus forming a proportional closed-loop controller.

Given the forgoing circuit description, the line scan rate is given by this equation:

Line Scan Rate    Equation 1

$$\frac{\text{scan\_line}}{\text{sec}} = \frac{\text{facets}}{\text{revolution}} \cdot \frac{1 \cdot \text{revolution}}{2 \cdot \text{cycle}} \cdot f_{poly}(\text{in\_Hz}) \frac{\text{cycle}}{\text{sec}}$$

Galvanometer Controller

The galvanometer provides the slow-scanning axis positioning mechanism. A line counter, maintained within the FPGA is added to a programmable offset value. This offset value allows the system to be mechanically aligned by the operator and PC keyboard rather than manually moving optics and mirrors to compensate for manufacturing tolerances. The result is fed to the vertical control DAC whose output voltage acts as the input to a position control, closed-loop servo. The galvanometer provides an optical position measuring mechanism that provides a ground-referenced bipolar output voltage that is proportional to angular position. The servo 240 drives the galvo coil with the difference between the vertical position DAC and measured angular position, thus forming a closed-loop, proportional position control servo.

Polygon Position (SOS) Detector

A secondary laser 244 is swept across a dual-photodetector 245. A comparitor circuit 247 whose output state is determined by the comparison of the two detector currents act as a physical start-of-scan (or SOS for short) reference signal. The comparitor is high when photodetector A's current is larger then B and low when B is larger than A's. Also, the exact polarity A>B, B>A only represents a digital signal inversion and is therefore somewhat insignificant. This signal is digitally delayed within the FPGA to become horizontal sync (HSYNC for short). Video capture boards synchronize data collection using this signal, insuring that the imaging laser is located at the same physical location for each scanned line.

Field Upoadable Firmware/FPGA Code

The microprocessor 222 has a diagnostic monitor mode that is activated by applying a specific monitor entry voltage to its IRQ pin and simultaneously pulsing the reset pin. A circuit is provided that allows the FPGA 227 to perform this function thus allowing the host PC to activate this mode of the microprocessor. During this mode, the external system has access to all registers and memory locations within the microprocessor's memory map. This mode is used to update the microprocessor's internal operating program (e.g. firmware) stored in on-board (inside the CPU) flash ROM.

Furthermore, FPGA operating code is stored in a non-volatile serial EEPROM. The microprocessor's I/O signals are directly connected to the reset, clock and data signals of the aforementioned EEPROM. By operating these signals in their three-state mode (e.g. by programming them to be inputs to the CPU), they do not interfere with FPGA load operations. Conversely, by placing the FPGA in its reset state, these signals are used to load new programs from microprocessor memory into the FPGA serial EEPROM. After which time, the FPGA can be reset causing it to load the new program data from the serial EEPROM.

From the foregoing description, it will be apparent that there has been provided an improved confocal imaging system including a confocal imaging head and associated apparatus. Variations in the system, the head, and the apparatus, within the scope of the invention, will undoubtedly become apparent to those skilled in the art. Accordingly, the foregoing description should be taken as illustrative and not in a limiting sense.

What is claimed is:

1. An apparatus for imaging of one or more selected locations of a body of a patient comprising:
    an imaging head having a confocal microscope with an objective lens having an optical axis, wherein said head has a projecting nose;
    an upright support station;
    a first mechanism attaching said head to said support station and providing a multiplicity of movements in horizontal and vertical displacement and in rotations of said head to position said head at said one or more selected locations;
    a second mechanism in said head enabling movement of said nose with respect to said objective lens in a plurality of directions generally perpendicular to the optical axis of the objective for fine positioning of said nose precisely at each of said one or more selected locations; and
    a third mechanism in said head for moving said objective lens in which said objective lens is movable by said third mechanism only along said optical axis of said objective lens, wherein said second mechanism and said third mechanism are operable separate from said first mechanism.

2. The apparatus according to claim 1 further comprising a manually accessible control panel mounted on said head and having controls for movement of said nose and said objective lens in X, Y and Z directions, respectively, by said second mechanism and third mechanism, respectively.

3. The apparatus according to claim 1 further comprising a handle extending from said head for manually moving said head using said first mechanism to said one or more selected locations.

4. The apparatus according to claim 1 wherein said first mechanism comprises a plurality of articulated arm sections.

5. The apparatus according to claim 4 wherein said first mechanism further comprises gimble joints which connect said arm sections to said support station and to said head, and a joint enabling rotational movement connecting said arm sections to each other thereby providing said multiplicity of movements.

6. The apparatus according to claim 1
    wherein said head is disconnectable from said first mechanism for independent movement.

7. The apparatus according to claim 6 wherein said head has a housing and a handle at one end of said housing providing a receptacle for receiving a connection at an end of said first mechanism in said receptacle in releasably latched relationship.

8. The apparatus according to claim 1 wherein said support station provides a platform for mounting a display for monitoring images produced by said confocal microscope.

9. The apparatus according to claim 8 further comprising an electronically controllable apparatus for interfacing with said display and said head to generate confocal microscope images of the cellular structure of said body at said locations.

10. The apparatus according to claim 1 wherein said support station is mounted on casters for movement thereof with said arm mechanism and head across a floor upon which the casters roll.

11. The apparatus according to claim 1 wherein said head comprises an integrated mechanical assembly of optical and electronic components for providing said confocal microscope.

12. The apparatus according to claim 11 wherein said assembly comprises a PCB (printed circuit board) and a chassis plate attached in general parallel relationship, said chassis plate providing a mounting for said optical components, in which said optical components mounted to said chassis plate have at least an optical scanning element, and said PCB providing a mounting for said electronic components.

13. The apparatus according to claim 12 wherein said PCB is disposed facing a side of said chassis plate opposite to the optical scanning element.

14. The apparatus according to claim 12 wherein said PCB has mounted thereon a plurality of circuits for providing programmed operation and control of said head and creating signals providing images of said body at said selected locations.

15. The apparatus according to claim 1 wherein said second mechanism and said third mechanism are operable separate from each other.

16. A confocal microscope imaging head comprising an integrated mechanical assembly of optical and electronic components in a common housing, and wherein said assembly comprises a printed circuit board (PCB) and a chassis plate attached in general parallel relationship, said chassis plate providing a mounting for said optical components, in which said optical components mounted to said chassis plate have at least an optical scanning element, and said PCB providing mounting for said electronic components, wherein said PCB is disposed facing a side of said chassis plate opposite to the optical scanning element.

17. The apparatus according to claim 16 wherein said PCB has mounted thereon a plurality of circuits for providing programmed operation and control of said head and creating signals providing images of selected locations of said body of a patient.

18. The apparatus according to claim 17 wherein said programmed operation has means for providing the ability to upgrade firmware and FPGA (field programmable gate array) program code under software control.

19. An apparatus for imaging tissue comprising:
a head comprising an projecting nose and imaging means for producing sectional images of tissue, said imaging means having optics comprising at least an objective lens;
an upright support station;
a first means attaching said head to said support station and providing a multiplicity of movements in horizontal and vertical displacement and in rotations of said head to position said head in contact with tissue to be imaged;
a second means in said head enabling movement of said nose with respect to said objective lens along X and Y orthogonal axes for fine positioning of said nose with respect to said objective lens; and
a third means in said head for moving said objective lens in which said objective lens is movable by said third means only along a Z axis orthogonal to said X and Y axes to enable said imaging means to focus at different depths in the tissue and thereby provide said sectional images at said different depths, wherein said first, second, and third means are each operable separate from each other.

* * * * *